US006482211B1

(12) United States Patent
Choi (10) Patent No.: US 6,482,211 B1
(45) Date of Patent: Nov. 19, 2002

(54) ANGULATED STENT DELIVERY SYSTEM AND METHOD OF USE

(75) Inventor: Steven B. Choi, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 80 days.

(21) Appl. No.: 09/628,852

(22) Filed: Jul. 31, 2000

(51) Int. Cl.[7] ................................................ A61F 11/00
(52) U.S. Cl. ................. 606/108; 623/1.11; 604/103.03; 604/103.05; 604/163; 604/165.01; 604/284; 604/171
(58) Field of Search .............................. 623/1.11, 1.12, 623/1.35, 23.64, 23.7; 606/108, 191, 192, 194, 195; 604/27, 28, 506–510, 93.01, 96.01, 103, 103.03, 103.05, 103.09, 163, 165.01, 171, 246, 523, 524, 284, 533, 905, 921

(56) References Cited

U.S. PATENT DOCUMENTS

| 4,994,071 | A | | 2/1991 | MacGregor |
| 5,607,444 | A | | 3/1997 | Lam |
| 5,613,980 | A | | 3/1997 | Chauhan |
| 5,669,924 | A | | 9/1997 | Shaknovich |
| 5,720,735 | A | | 2/1998 | Dorros |
| 5,749,825 | A | | 5/1998 | Fischell et al. |
| 5,871,536 | A | | 2/1999 | Lazarus |
| 5,893,887 | A | | 4/1999 | Jayaraman |
| 6,001,124 | A | | 12/1999 | Bachinski |
| 6,048,361 | A | | 4/2000 | Von Oepen |
| 6,051,020 | A | | 4/2000 | Goicoechen et al. |
| 6,090,133 | A | | 7/2000 | Richter et al. |
| 6,099,497 | A | * | 8/2000 | Adams et al. ......... 604/101.01 |
| 6,099,560 | A | | 8/2000 | Penn et al. |
| 6,165,195 | A | | 12/2000 | Wilson et al. |
| 6,221,098 | B1 | | 4/2001 | Wilson et al. |
| 6,254,593 | B1 | * | 7/2001 | Wilson ....................... 623/1.11 |
| 6,287,277 | B1 | * | 9/2001 | Yan ............................. 604/916 |

FOREIGN PATENT DOCUMENTS

| EP | 0 891 751 A1 | 1/1999 |
| EP | 0 897 700 A1 | 2/1999 |
| EP | 0 965 311 A2 | 12/1999 |

OTHER PUBLICATIONS

Whitlow, Patrick L., Chapter 17: Ostial and Bifurcation Lesions, *Textbook of Inventional Cardiology*, Edited by S. Topol, pp. 317–334, (Undated).
Application for U.S. Letters patent Ser. No. 08/910,857 filed Aug. 13, 1997.
Application for U.S. Letters patent Ser. No. 09/412,113 filed Oct. 5, 1999.

* cited by examiner

Primary Examiner—David J. Isabella
Assistant Examiner—Urmi Chattopadhyay
(74) Attorney, Agent, or Firm—Fulwider Patton Lee & Utecht, LLP (57) ABSTRACT

An improved catheter assembly and method are provided for delivering angulated stents to a diseased vessels. The assembly allows for the precise delivery of an angulated stent into a side branch vessel that is at varying angles with respect to a main vessel. The assembly includes a single balloon Y-shaped balloon catheter having a restraining member attached to the distal section of the catheter to assist in proper delivery of the angulated stent. The restraining member of the catheter assembly of the present invention is configured to prevent the deployment of an angulated stent unless proper orientation of catheter assembly is first achieved. Because a pre-mounted stent is oriented to coincide with the diseased side branch vessel, once proper orientation of the catheter assembly is achieved, deployment of the angulated stent will be precise.

18 Claims, 9 Drawing Sheets

ANGULATED STENT DELIVERY SYSTEM AND METHOD OF USE

BACKGROUND OF THE INVENTION

The present invention relates to a stent delivery system for use at a vessel bifurcation. More particularly, the present invention relates to a catheter assembly and method for assisting in the accurate delivery of an angulated stent into an acutely angulated side branch vessel for treatment thereof in a percutaneous transluminal coronary angioplasty (PTCA) procedure.

Stents conventionally repair blood vessels that are diseased. Stents are generally hollow and cylindrical in shape and have terminal ends that are generally perpendicular to their longitudinal axes. In use, the conventional stent is positioned at the diseased area of a vessel and, after placement, the stent provides an unobstructed pathway for blood flow.

Repair of vessels that are diseased at a bifurcation is particularly challenging since the stent must overlay the entire diseased area at the bifurcation, yet not itself compromise blood flow. Therefore, the stent must, without compromising blood flow, overlay the entire circumference of the ostium to a diseased portion and extend to a point within and beyond the diseased portion. Where the stent does not overlay the entire circumference of the ostium to the diseased portion, the stent fails to completely repair the bifurcated vessel. Where the stent overlays the entire circumference of the ostium to the diseased portion, yet extends into the junction comprising the bifurcation, the diseased area is repaired, but blood flow may be compromised in other portions of the bifurcation. Unopposed stent elements may promote lumen compromise during neointimalization and healing, producing restenosis and requiring further procedures. Moreover, by extending into the junction comprising the bifurcation, the stent may block access to portions of the bifurcated vessel that require performance of further interventional procedures. Similar problems are encountered when vessels are diseased at their angled origin from the aorta as in the ostium of a right coronary or a vein graft. In this circumstance, a stent overlaying the entire circumference of the ostium extends back into the aorta, creating problems, including those for repeat catheter access to the vessel involved in further interventional procedures.

Conventional stents are designed to repair areas of blood vessels that are removed from bifurcations and, since a conventional stent generally terminates at right angles to its longitudinal axis, the use of conventional stents in the region of a vessel bifurcation may result in blocking blood flow of a side branch or fail to repair the bifurcation to the fullest extent necessary. The conventional stent might be placed so that a portion of the stent extends into the pathway of blood flow to a side branch of the bifurcation or extend so far as to completely cover the path of blood flow in a side branch. The conventional stent might alternatively be placed proximal to, but not entirely overlaying, the circumference of the ostium to the diseased portion. Such a position of the conventional stent results in a bifurcation that is not completely repaired. The only conceivable situation in which the conventional stent, having right-angled terminal ends, could be placed where the entire circumference of the ostium is repaired without compromising blood flow, is where the bifurcation is formed of right angles. In such scenarios, extremely precise positioning of the conventional stent is required. This extremely precise positioning of the conventional stent may result with the right-angled terminal ends of the conventional stent overlaying the entire circumference of the ostium to the diseased portion without extending into a side branch, thereby completely repairing the right-angled bifurcation.

To circumvent or overcome the problems and limitations associated with conventional stents in the context of repairing diseased bifurcated vessels, an angulated stent that consistently overlays the entire circumference of the ostium to a diseased portion, yet does not extend into the junction comprising the bifurcation, may be employed. Unlike the conventional stents described above which terminate at right angles to its longitudinal axis, an angulated stent terminates at various angles depending upon and corresponding to the angulation of the bifurcated ostium. An angulated stent is designed to match the angle of the ostium of the branch and therefor offers maximum coverage. An angulated stent would have the advantage of completely repairing the vessel at the bifurcation without obstructing blood flow in other portions of the bifurcation. In addition, such a stent would allow access to all portions of the bifurcated vessel should further interventional treatment be necessary. In a situation involving disease in the origin of an angulated aorto-ostial vessel, such a stent would have the advantage of completely repairing the vessel origin without protruding into the aorta or complicating repeat access.

In addition to the problems encountered by using the prior art stents to treat bifurcations, the delivery platform for implanting angulated stents has presented numerous problems. The major issues for this type of delivery system are centered on the translational and rotational orientation of the stent at the time of deployment. As current stent and delivery systems are used to treat these lesions, the translation problem of locating the stent precisely at the ostium is compounded by the effect of improper placement. Current methods for conventional stent placement rely heavily on the catheter design, which has been shown to be relatively effective in straight or non-branched anatomy. However, in areas of bifurcation these conventional methods have proven to be less effective.

Because an angulated stent is designed to match the angle of the ostium of the branch, proper rotational orientation is critical. While visualizing the delivery system is not a critical issue, precise positioning of the angulated stent in a specific location, such as a carina, using two dimensional images of a three dimensional anatomy poses a tremendous challenge.

One prior art device used to deliver an angulated stent is a bifurcation lesion stent system that utilizes a dual guide wire catheter for placement of an angulated stent. An angulated stent is pre-mounted on a balloon and is delivered over a routine angioplasty guide wire, the tracking guide wire, down the side branch allowing the stent system to track down the branch. A second positioning guide wire is placed down a separate lumen and on the balloon surface such that it turns away from the balloon at an angle just proximal to the stent. Once located at a bifurcation, the tracking wire is advanced down the side branch and the stent positioning guide wire is advanced down the primary vessel. Once the stent delivery balloon has been positioned in the branch vessel, then the stent is positioned in an appropriate position at the ostium of the side branch. The stent is deployed at the ostium of the side branch using the positioning wire to ensure optimal location of the stent. If the stent were misaligned with the ostium of the side branch, the positioning wire would provide torque on the delivery catheter and would not allow advancement of the balloon into the correct position unless the stent system were rotated appropriately.

Attempts to deliver any device, such as an angulated stent on a balloon assembly to a bifurcation over two wires are prone to the problem of wire wrapping. The resulting wrapping then creates resistance to advancement of the device, thus resulting in failure of deployment. Therefore, when delivering a device ultimately utilizing two wires, it would be desirable to first achieve proper rotational orientation prior to entrance into the target vessel. The present invention offers a solution to these problems and others.

As used herein, the terms "proximal," "proximally," and "proximal direction" when used with respect to the invention are intended to mean away from or out of the patient, and the terms "distal," "distally," and "distal direction" when used with respect to the invention are intended to mean toward or into the patient. These definitions will apply with reference to apparatus, such as catheters, guide wires, stents, and the like.

What is needed and heretofore unavailable is a catheter assembly that allows for accurate placement and deployment of an angulated stent in an acutely angulated side branch vessel at a bifurcation. The present invention satisfies these and other needs.

SUMMARY OF THE INVENTION

The invention provides for an improved catheter assembly and method of use for assisting in the delivery of an angulated stent into an acutely angulated side branch vessel for the purpose of accurate placement of the angulated stent. The catheter assembly of the present invention has the feature of containing, in addition to a deployment guide wire, a positioning guide wire and restraint mechanisms that physically permit precise positioning of the angulated stent for deployment.

In one aspect of the invention, there is provided an angulated stent delivery catheter assembly that includes a Y-shaped balloon catheter. The catheter assembly proximal section (the trunk of the Y-shape) includes a catheter tube having a positioning guide wire lumen, an inflation lumen and an elongate tubular member. The elongate tubular member includes a deployment guide wire lumen. The inflation lumen of the catheter proximal section may be configured in a number of ways. For example, the inflation lumen may be configured as an annular lumen positioned concentrically about the elongate tubular member such that the elongate tubular member's outer surface and the inner surface of the catheter tube form an annular inflation lumen. Alternatively, the inflation lumen may be positioned in a side-by-side configuration with the deployment lumen and the positioning lumen.

The catheter assembly distal section (the branches of the Y-shape) includes a positioning tube (the first branch) and a deployment tube (the second branch). The positioning tube includes a guide wire lumen. The deployment tube may include an elongate tubular member having a guide wire lumen, and an expandable member circumferentially placed about the elongate tubular member. Together, the outer surface of the elongate tubular member and the inner surface of the expandable member define an inflation cavity. An angulated stent may be positioned over the expandable member.

A restraining member is positioned at the catheter assembly distal section and is associated with the deployment tube and positioning tube so that, as the catheter is positioned near a target site in the body lumen, the restraining member assists in properly orienting and maneuvering the deployment tube with the angulated stent positioned thereon into a diseased side branch vessel. The restraining member may have a U-shaped configuration, and may be attached to the positioning tube such that it encompasses the deployment tube and serves to restrict movement of the deployment tube to a predetermined direction. Alternatively, the restraining member may be a sheath having a slit. The sheath may be attached to envelop the entire distal section of the catheter assembly, and the slit may be positioned on the side of the sheath that corresponds to the deployment tube, thereby restricting movement of the deployment tube to a predetermined direction.

In another aspect of the invention, there is provided a method of positioning and deploying an angulated stent into an acutely angulated side branch vessel for treatment of that diseased vessel. The method includes the steps of providing a Y-shaped balloon catheter assembly configured with a positioning tube having a positioning guide wire lumen, a deployment tube having an elongate tubular member including a deployment guide wire lumen, and having an expandable member, and a restraining member. An angulated stent may be mounted on the expandable member of the deployment tube in an orientation that corresponds with the orientation of a diseased side branch vessel. A positioning guide wire may be disposed within the positioning tube, and a deployment guide wire may be disposed within the deployment tube. The positioning guide wire may be introduced into the patient's vasculature and delivered to a diseased target site within the main vessel. The catheter assembly may be delivered over the positioning guide wire until the catheter distal section is positioned near or at the diseased target site within the main vessel. If necessary, the catheter may be rotated into a desired orientation within the main vessel to align the stent with the orientation of a diseased side branch vessel at the diseased target site. The deployment guide wire may then be maneuvered into the diseased side branch vessel at the target site. Thereafter, the deployment tube may be further advanced over the deployment wire into the side branch vessel. Once the stent is positioned at the target site, the expandable member may be expanded by injecting inflation fluid into the cavity of the expandable member, to deploy the angulated stent. Where subsequent treatment may be required, withdrawal of the catheter and the positioning guide wire allows the deployment guide wire to remain in the side branch providing side branch access for any additional interventional treatment to that vessel. Withdrawal of the catheter with both the positioning and deployment guide wires left in the vessel permits the subsequent use of these two unwrapped wires, should further intervention requiring two wires be necessary.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

As shown in the exemplary drawings wherein like reference numerals indicate like or corresponding elements among the figures, the present invention includes an improved catheter assembly and method of use in the delivery of an angulated stent into an acutely angulated side branch vessel for the purpose of proper deployment of the angulated stent.

Figure 1:
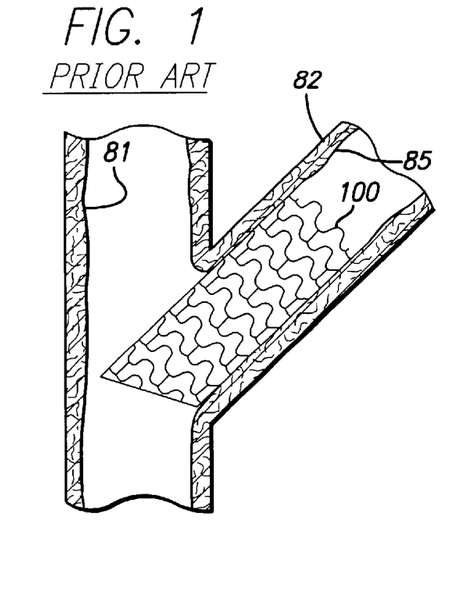
FIG. 1 is an illustration of an improperly deployed prior art angulated stent, wherein the stent protrudes into a main vessel.
Figure 2:
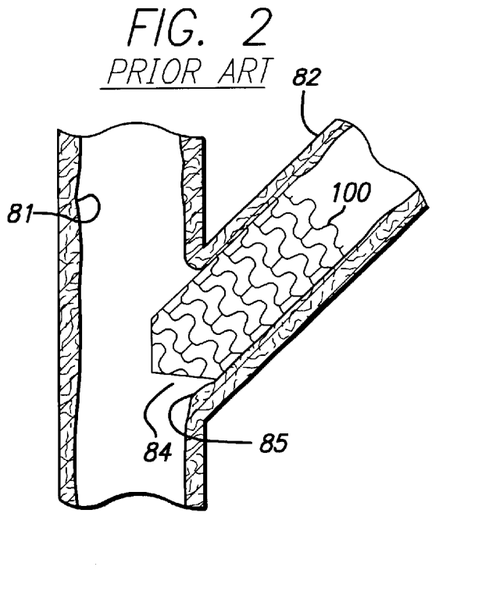
FIG. 2 is an illustration of an improperly deployed prior art angulated stent, wherein the stent protrudes into a main vessel and there are diseased areas of a side branch vessel that are uncovered.
Figure 3:
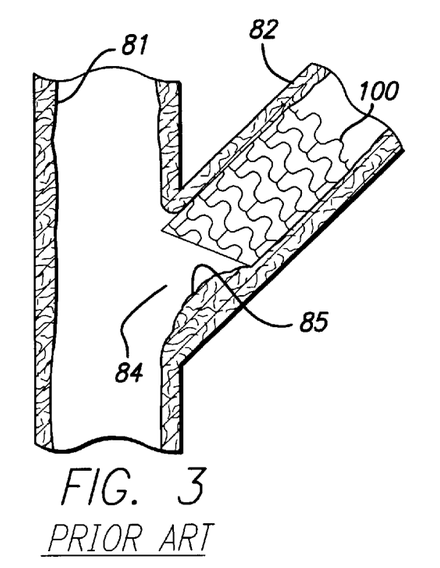
FIG. 3 is an illustration of an improperly deployed prior art angulated stent, wherein there are areas of a diseased side branch vessel that are uncovered.
Figure 4:
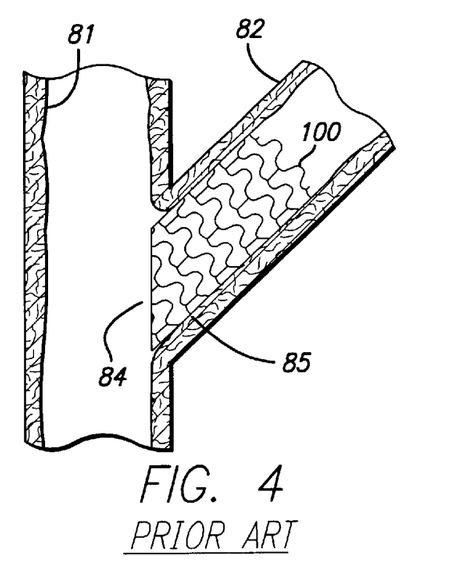
FIG. 4 is an illustration of a properly deployed prior art angulated stent in a side branch vessel, wherein the stent does not protrude into a main vessel and there are no uncovered diseased areas of the side branch vessel.

Because an angulated stent is designed to match the angle of the ostium of the branch, proper rotational orientation is critical. Precise positioning of the angulated stent in a specific location, such as a carina, using two dimensional images of a three dimensional anatomy poses a tremendous challenge. Prior art attempts at delivering an angulated stent to a bifurcation have proven to be cumbersome and less than satisfactory. Referring to FIGS. 1–3, improper orientation and placement of an angulated stent 100 at the target site 84 will result in adverse deployment conditions. For example, one adverse deployment condition is when a portion of the deployed angulated stent extends into the main vessel 81 (FIG. 1), another is when a portion of the angulated stent extends into the main vessel and diseased portions 85 of the side branch vessel 82 remain exposed (FIG. 2) or another where the angulated stent does not extend into the main vessel, but diseased portions of the side branch vessel remain exposed (FIG. 3). Any of these conditions resulting from improper orientation and placement of the angulated stent will be more detrimental than beneficial. Referring to FIG. 4, proper orientation and placement of the angulated stent will result in full coverage of the diseased portions of the side branch vessel and minimal if any extension of the angulated stent into the main vessel.

Turning to FIGS. 5–11, in one embodiment of the present invention, a two guide wire catheter assembly 70 is configured to provide proper orientation of an angulated stent 100 so that once the catheter is properly positioned at a target area 84 of a main vessel 81, deployment of the angulated stent into a side branch vessel 82 is accurately achieved. As shown in FIG. 5A, the catheter assembly may be configured as a single balloon Y-shaped balloon catheter having a proximal end 115 and a distal end 116. The catheter assembly includes a proximal section 72 having a catheter tube 69 and a distal section 74 having a positioning tube 23 and a deployment tube 30, such that the catheter tube of the catheter proximal section comprises the "trunk" of the Y-shape catheter and the positioning tube and deployment tube of the catheter distal section comprises the "branches" of the Y-shape catheter. The catheter proximal section is connected to the distal section at a Y-junction 73, thereby forming the Y-shape. The catheter tube 69 includes a positioning wire lumen 76 having a proximal section 75 and a distal section 77, an elongate tubular member 37 having a proximal section 36 and a distal section 38, and an inflation lumen 40. The elongate tubular member includes a deployment guide wire lumen 79 having a proximal section 78 and a distal section 80.

Figures 5A, 5B:
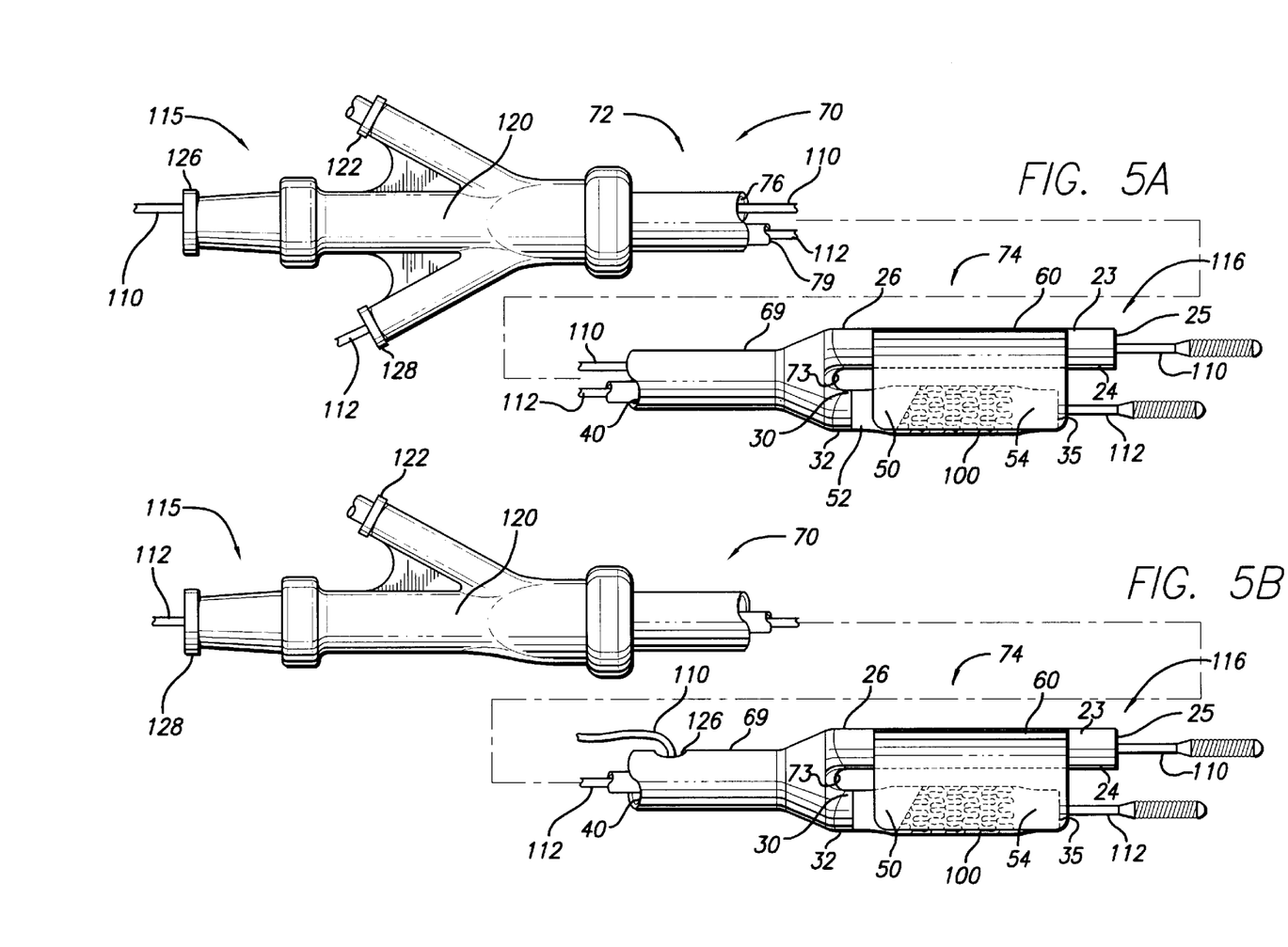
FIG. 5A is a longitudinal plan view of one embodiment of a catheter assembly including a U-shaped restraining member of the present invention, wherein the catheter is embodied in an over-the-wire configuration for receiving both a positioning guide wire and a deployment guide wire.
FIG. 5B is a longitudinal plan view of one embodiment of a catheter assembly including a U-shaped restraining member of the present invention, wherein the catheter is embodied in an over-the-wire configuration for receiving a deployment guide wire and in a rapid exchange configuration for receiving a positioning guide wire.

The catheter tube 69 encompasses the positioning wire lumen proximal section 75, the elongate tubular member proximal section 36, the deployment guide wire lumen proximal section 78 and the inflation lumen 40. Additionally, the catheter tube's proximal end connects to a sidearm 120 that includes a positioning guide wire port 126 that connects to the positioning wire lumen 76, a deployment guide wire port 128 that connects to a deployment wire lumen 79, and an inflation port 122 that provides an inlet to the inflation lumen 40 of the catheter. The positioning guide wire port and the deployment guide wire port enable a positioning guide wire 110 and a deployment guide wire 112 to enter and exit from the proximal end of the catheter assembly for an over-the-wire configuration (FIG. 5A).

It will be apparent to one of ordinary skill in the art that the catheter assembly 70 as described herein can have either an over-the-wire ("OTW") or rapid exchange (Rx) configuration as more fully disclosed in, but not limited to, U.S. Pat. No. 4,323,071 (Simpson et al.) (OTW); U.S. Pat. No. 4,573,470 (Samson et al.) (OTW); U.S. Pat. No. 5,501,227 (Yock) (Rx); U.S. Pat. No. 5,061,273 (Yock) (Rx); and U.S. Pat. No. 5,496,346 (Horzewski et al.) (Rx). As shown in FIG. 5A, the catheter assembly 70 may be configured as an over-the-wire intravascular catheter. Alternatively, the catheter assembly 70 may be configured for use in rapid exchange configurations. Either one or both of the positioning guide wire and/or the deployment guide wire may be delivered in a Rx configuration. For example, as shown in FIG. 5B, the positioning guide wire 110 is in an Rx configuration and the deployment guide wire 112 is in an OTW configuration, the catheter proximal section's 72 proximal end connects to a sidearm 120 that includes an inflation port 122 providing an inlet to the inflation lumen 40 of the catheter. The sidearm also includes a deployment guide wire port 128 that connects to a deployment wire lumen 79 to enable a deployment guide wire 112 to enter and exit from the proximal end of the catheter assembly for over-the-wire mode of operation. For Rx mode of operation, a positioning guide wire port 126 is positioned on the catheter proximal section at a location proximal to the Y-junction 73. The positioning guide wire port enables a positioning guide wire to enter and exit the catheter assembly for Rx mode of operation.

Although either OTW or Rx mode of operation may be interchangeable for delivery of each of the positioning guide wire or deployment guide wire, it is advantageous that the deployment guide wire be utilized in conjunction with OTW mode of delivery. Having the deployment guide wire delivered in OTW mode may prevent the problems associated with wire wrapping.

Referring to FIGS. 6–9, the distal end of the catheter proximal section 72 is connected to and communicates with the proximal end of the catheter distal section 74 at a Y-junction 73. There are substantially continuous lumens for each of the positioning guide wire lumen 76, the deployment guide wire lumen 79, and the inflation lumen 40 that extend throughout the entirety of the Y-shaped balloon catheter.

The catheter distal section 74 is comprised of two "branches" of the Y-shaped catheter, the first "branch" of the catheter distal section is a positioning tube 23 having a proximal end 26 and a distal end 24. The distal end of the positioning tube has a positioning tube end port 25. The second "branch" includes a deployment tube 30 having a proximal end 32 and a distal end 34. The distal end of the deployment tube is configured with a deployment tube end port 35.

Figures 6, 7, 8, 9:
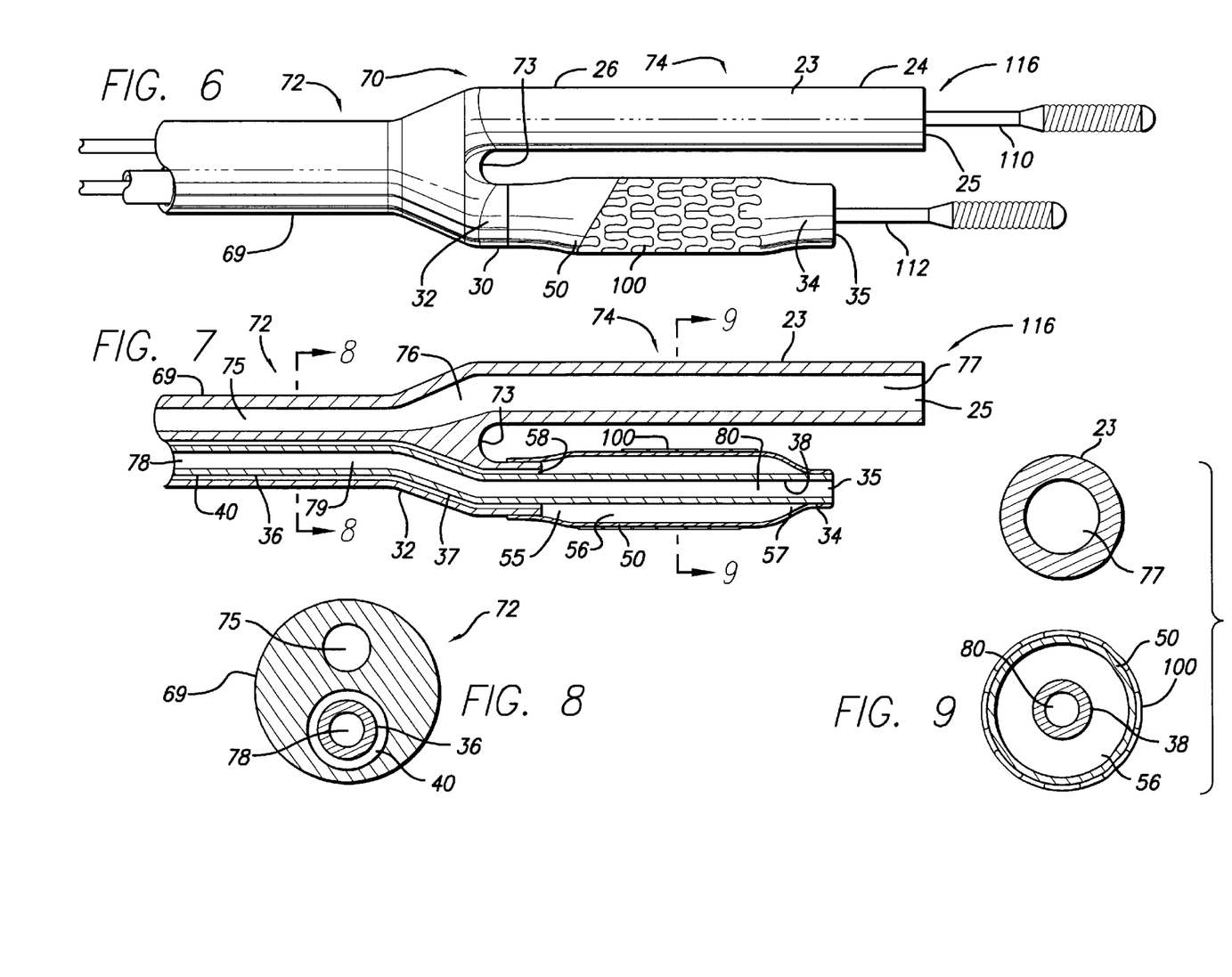
FIG. 6 is a longitudinal plan view of a catheter distal section of FIG. 5A, without the restraining member.
FIG. 7 is a longitudinal cross-sectional view of the catheter distal section of FIG. 6, wherein an elongate tubular member is disposed within an inflation lumen.
FIG. 8 is a transverse cross-sectional view of the catheter proximal section of FIG. 7 taken along lines 8—8.
FIG. 9 is a transverse cross-sectional view of a catheter distal section of FIG. 7 taken along lines 9—9.

As shown in FIGS. 7–9, the positioning tube 23 (the first "branch") includes the positioning wire lumen distal section 77. The positioning wire lumen 76 is a single continuous lumen, which may extend throughout the entire catheter assembly 70, such that the positioning wire lumen proximal section 75 extends throughout the catheter proximal section 72, and the positioning wire lumen distal section extends throughout the catheter distal section 74. Additionally, the positioning tube includes an end port 25 at the distal extremity of the positioning tube that allows a positioning guide wire 110 to exit the catheter assembly. The positioning wire lumen 76 is configured to receive a positioning guide wire 110. The positioning guide wire continuously extends through both the catheter positioning wire lumen of the catheter proximal section and the positioning tube lumen of the catheter distal section where it exits from the distal end of the positioning tube at the positioning tube end port located at the distal end of the positioning tube.

The deployment tube 30 (the second "branch") includes the elongate tubular member distal section 38, the deployment wire lumen distal section 80 and an expandable member 50. The elongate tubular member may extend throughout the entire catheter, providing a continuous deployment guide wire lumen that may extend throughout the catheter proximal section 72 and distal section 74. The deployment guide wire lumen of the elongate tubular member is configured to receive a deployment guide wire 112. The deployment guide wire continuously extends from a deployment wire lumen 78 of the catheter proximal section through the deployment wire lumen 80 of the catheter distal section, where it exits from the distal end of the elongate tubular member of the deployment tube 30 at the deployment tube end port 35 located at the distal end of the deployment tube.

The positioning guide wire 110 is preferably a stiff wire having a diameter of about 0.036 millimeters (mm) (0.014 inch). The deployment guide wire 112 is preferably a flexible "front-line" type wire, such as a "high torque" or "balanced mid. weight" wire which is typically used in dilatation procedures. However, as one of ordinary skill in the art will appreciate, a number of guide wire configurations may be used as required for a particular application, such as guide wires having different diameters and degrees of stiffness. Particularly suitable guide wires can include those manufactured and sold under the tradenames SPORT and IRONMAN, manufactured by Advanced Cardiovascular Systems, Inc., Santa Clara, Calif.

The two branches—the positioning tube 23 and the deployment tube 30—are configured to reside side-by-side (Y-shaped) for low profile delivery, wherein the deployment tube may be capable of moving away from the side-by-side position next to the positioning tube. An angulated stent 100 may be removably mounted on the expandable member 50 of the deployment tube.

An expandable member 50 may be formed or attached to the distal section of the deployment tube by any known method of adhesion, for example by heat bonding. The expandable member includes a proximal end 52 and a distal end 54 (FIGS. 5A and 5B). Additionally, the expandable member includes a cavity 56 having a proximal end 55 and a distal end 57, and is defined by the space between the expandable member and the elongate tubular member (FIG. 7). The proximal end of the expandable member includes a port 58, and the distal end 54 of the expandable member may be sealed off by a closed connection to the elongate tubular member 37 at a distal location slightly proximal to the deployment tube end port 35. The expandable member is in fluid communication with the distal end of the inflation lumen 40 through the expandable member port such that inflation fluid may be delivered into the expandable member cavity from the inflation lumen. The inflation lumen extends from the inflation port 122 in the sidearm 120 of the catheter proximal section 72 to the expandable member port 58 in the catheter distal section 74.

Figures 10, 11:
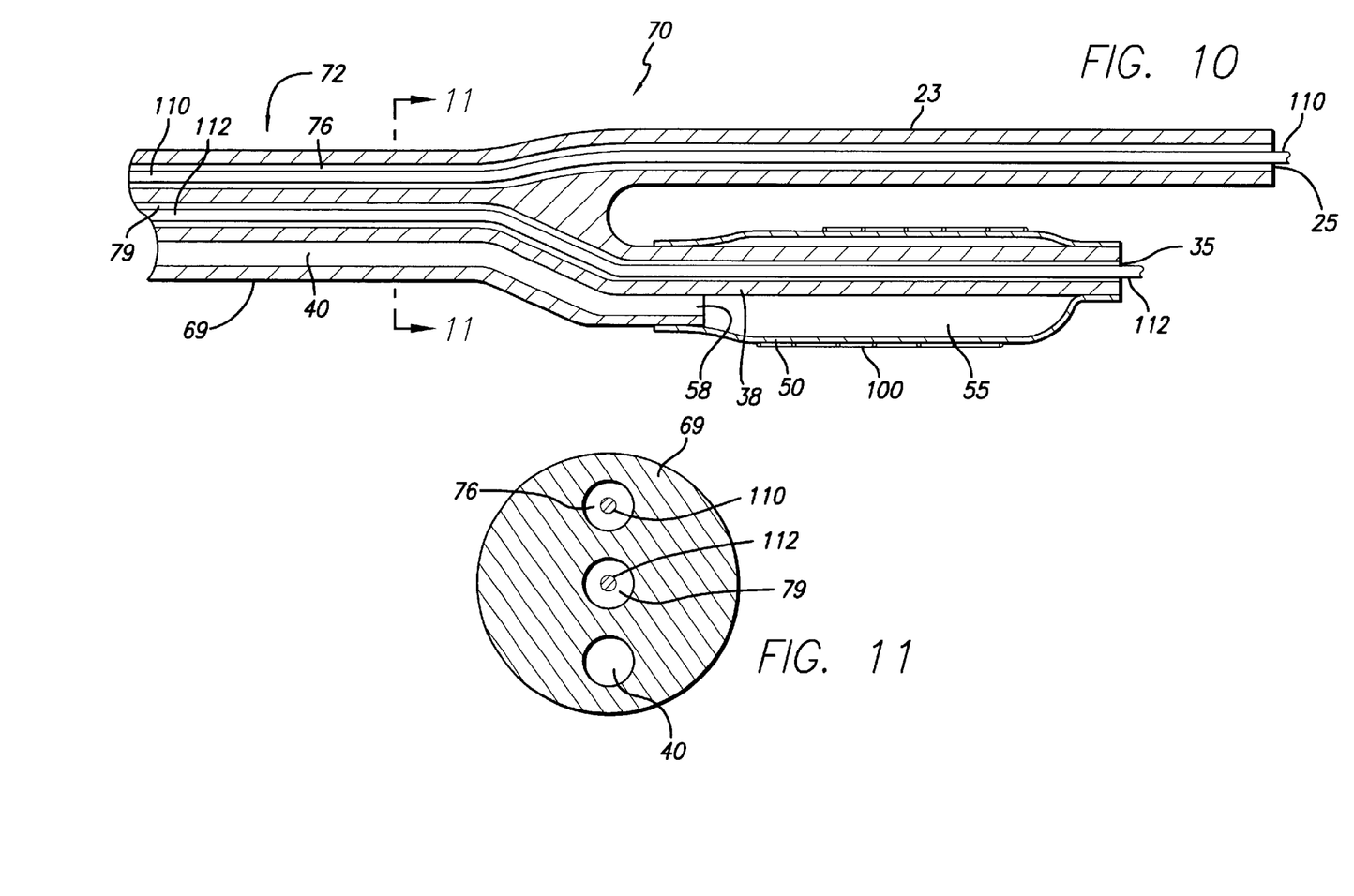
FIG. 10 is a longitudinal cross-sectional view of a catheter distal section, depicting an alternative configuration of FIG. 6, wherein an inflation lumen, a positioning guide wire lumen and a deployment guide wire lumen are configured side-by-side.
FIG. 11 is a transverse cross-sectional view of the catheter proximal section of FIG. 10 taken along lines 11—11.

It is noted that in the catheter proximal section 72, the inflation lumen 40 may be configured in a variety of ways. The inflation lumen may be configured as an outer lumen, wherein the elongate tubular member 37 and the deployment wire lumen 79 are concentrically disposed within the inflation lumen (as shown in FIGS. 7 and 8). Alternatively, the inflation lumen may be configured as an independent lumen positioned side-by-side with the deployment wire lumen (as shown in FIGS. 10 and 11). It will be apparent to one of ordinary skill in the art that the placement and configuration of the inflation lumen within the catheter proximal section may be of different variations without departing from the scope and functionality of the inflation lumen.

Figure 12:
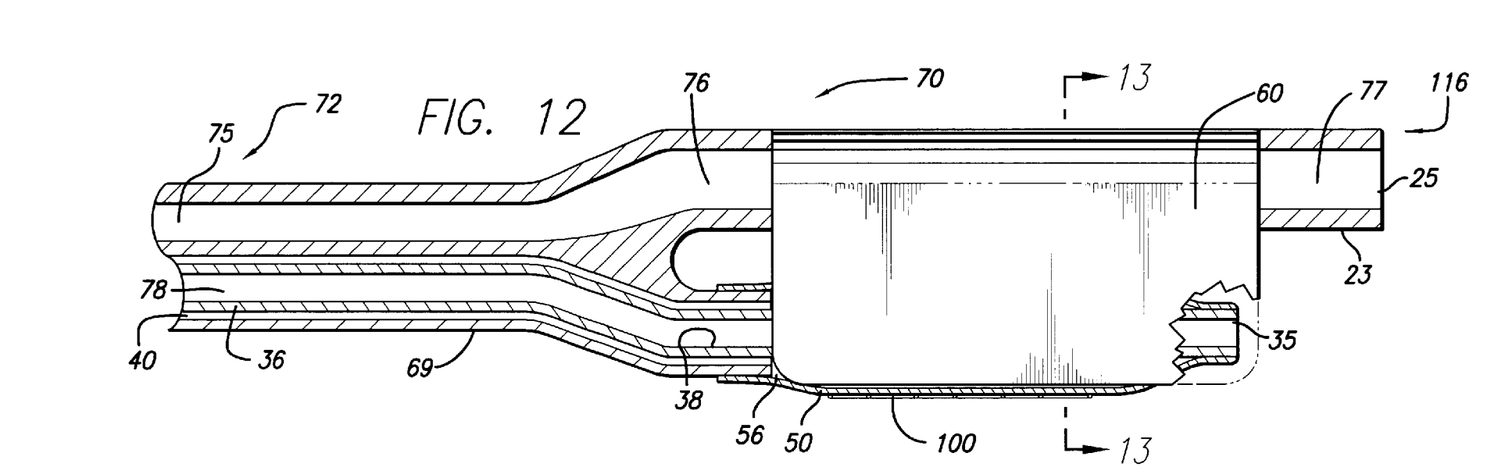
FIG. 12 is a longitudinal view, partially in cross-section, of a catheter distal section of FIG. 5A, including the U-shaped restraining member.

Referring to FIG. 12, the catheter distal section 74 further comprises a restraining member, such as a U-shaped member 60, fixed to the catheter distal section. The U-shaped member physically restricts lateral movement of the deployment tube 30 to a specific direction upon placement of catheter distal section within a patient's vasculature. The restricted lateral movement enforced by the U-shaped member ensures that the pre-mounted angulated stent 100 will not be deployed unless and until proper orientation of the catheter distal section is achieved. The U-shaped member may be formed from known catheter materials, such as Nylon 12 which provides both stiffness and flexibility. However, it is understood that other nylons or other polyamides, stiff polyesters, low density polyethelynes or polyurethanes may also be suitable. Such materials will provide both stiffness and flexibility for the desired application. The chosen Nylon 12 may be cut and shaped into a U-shape having a length adequate to cover a chosen angulated stent, for example the U-shape member may be cut with a length of fifty millimeters for an angulated stent of the same length, and a width of approximately one and one half to two mm and a thickness of about 0.01 mm to 0.2 mm. Additionally, the U-shaped member may be formed such that there are no squared or angulated edge comers, instead, the comers may be rounded to prevent vessel trauma during delivery and retraction of the catheter distal section 74. Once formed, the U-shaped member may be fixed to the catheter distal section by permanently attaching it to the positioning tube 23, using any suitable means of adhesion, such as heat bonding or gluing.

Figure 13:
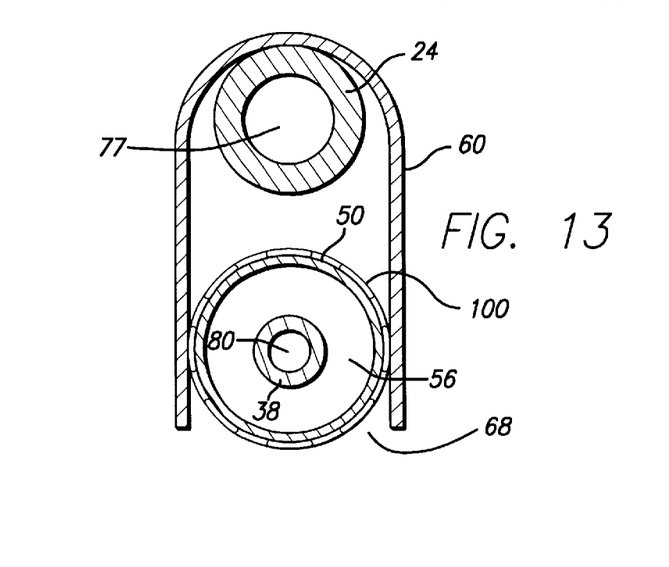
FIG. 13 is a transverse cross-sectional view of a catheter distal section of FIG. 12 taken along lines 13—13.

As shown in FIG. 13, The U-shaped member 60 is attached to the positioning tube 23 to encompass and restrict lateral movement of the deployment tube 30. The U-shaped member may be permanently fixed to the positioning tube and oriented to encompass the angulated stent 100, expandable member 50 and the deployment tube. In this configuration, the deployment tube will only be able to depart laterally in a single predetermined direction— laterally out of an opening 68 of the U-shaped member. Therefore, where the angulated stent 100 is pre-mounted in a position that coincides with the correct branch vessel lumen position, if the deployment tube 30 is free to move into the branch vessel, the angulated stent will be in the correct position for deployment.

Figures 14, 15, 16:
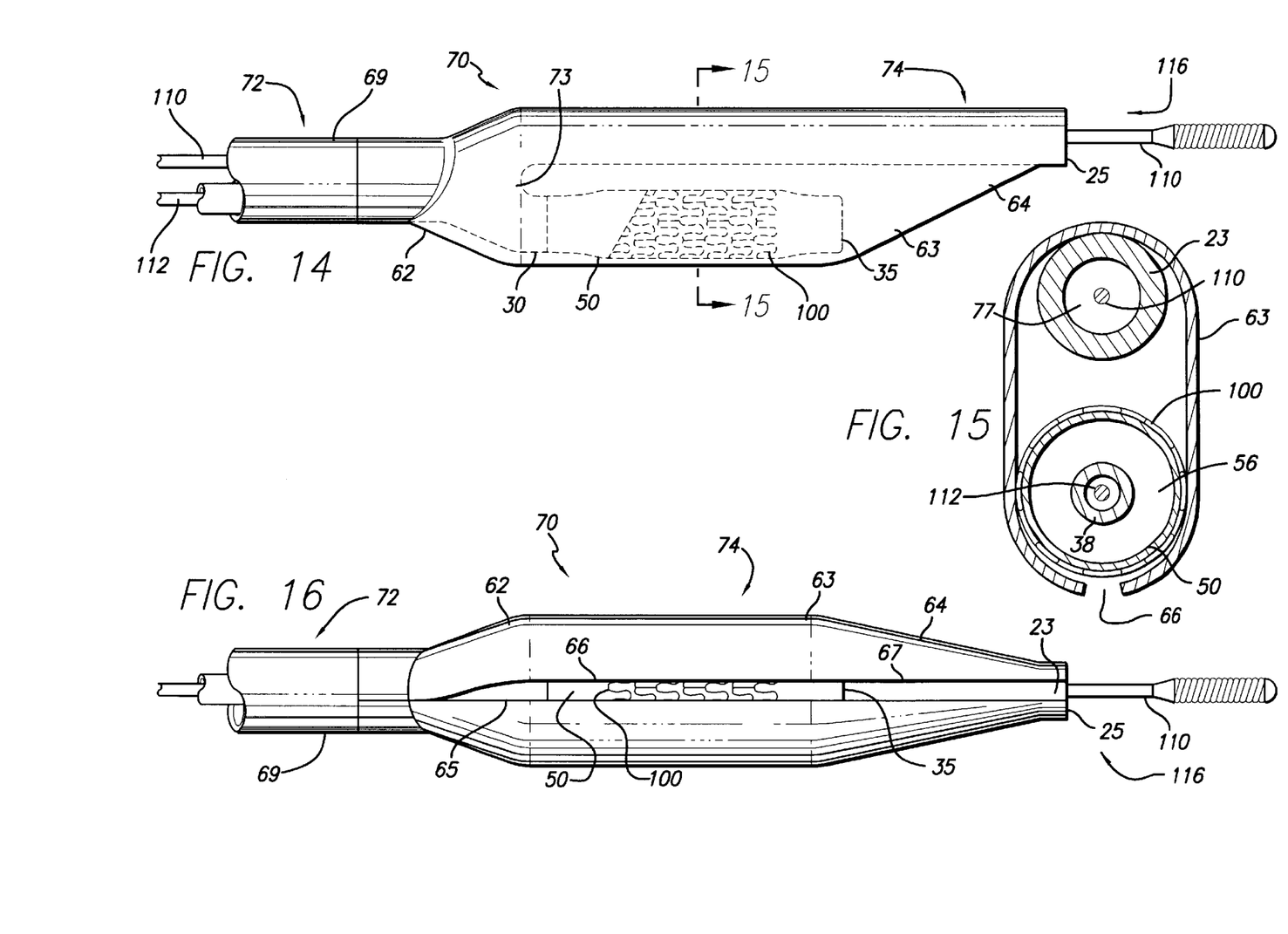
FIG. 14 is a longitudinal plan side view of an alternative embodiment of a catheter assembly including a sheath restraining member of the present invention, wherein a positioning tube, deployment tube, expandable member and stent are shown in hidden view.
FIG. 15 is a transverse cross-sectional view of a catheter distal section taken along lines 15—15 of FIG. 14, depicting the sheath restraining member having a slit.
FIG. 16 is a longitudinal plan bottom view of a catheter distal section of FIG. 14, depicting a slit in the sheath restraining member.

Referring to FIGS. 14–16, an alternative embodiment of the catheter assembly 70 of the current invention includes a restraining member in the form of a sheath 63 having a slit 66 for allowing lateral extension of the deployment tube 30. As shown in FIG. 14, the Y-shaped balloon catheter includes a distal section 74 having a restraining member in the form of a sheath extending substantially throughout the entire distal section. The sheath includes a proximal end 62 and a distal end 64. The sheath may be fixed to the catheter distal section, and envelops both the positioning tube 23 and deployment tube. The sheath slit includes a proximal end 65 and a distal end 67. The slit may extend throughout a major portion of the sheath such that the slit proximal end may be located at a position slightly distal of the sheath proximal end and may extend to the sheath distal end. Additionally, the slit may be positioned on the side of the sheath that corresponds to the location of the deployment tube.

The sheath 63 physically restrains lateral movement of the deployment tube 30 to a specified direction dictated by the position of the slit 66. The sheath serves similar restraining functions as the U-shaped member 60 of the embodiment described above. Because the sheath encompasses the positioning tube 23 and the deployment tube having the expandable member 50 and an angulated stent 100 mounted on the expandable member of the deployment tube, the deployment tube will only be able to depart laterally in a single predetermined direction that corresponds to the location of the slit. Therefore, where the angulated stent is mounted on the expandable member in a position that coincides with the correct branch vessel lumen position and orientation, if the deployment tube is free to move out of the slit and into the branch vessel, then the angulated stent will be in the correct position and orientation for deployment.

Several possible materials can be utilized to manufacture the sheath 63 in accordance with the present invention. These materials may include fluorinated ethylene-propylene resins (FEP), polytetrafluoroethylene (PTFE) fluoropolymers (TEFLON), polyethylene terephthalate (PET), Hytrel polyesters, aromatic polymers, or particularly polyethereketone (PEEK). Other materials include block co-polymers, particularly polyamide/polyester block co-polymers with a tensile strength of at least 6,000 psi and an elongation of at least 300%, and polyamide or nylon materials, such as Nylon 12, with a tensile strength of at least 15,000 psi.

Once the material has been selected, it can be extruded into a length of tubing using standard techniques known in the art. For example, in one method of extrusion, the tubing may then be heated and biaxially stretched in a glass or a metal mold until the desired wall thickness of 0.005 to 0.01 mm is achieved. The mold is then cooled and the thin wall tube is removed and cut to the appropriate length, typically, a length adequate to cover the catheter distal section 74.

Referring to FIGS. 17–22, in keeping with one method of use for the current invention, an angulated stent 100 is mounted and crimped onto the expandable member 50 of the deployment tube 30 of the catheter distal section 74 in an orientation that coincides with the orientation of a side branch vessel 82 of a patient's vasculature. The distal end of a positioning guide wire 110 is advanced into a main vessel 81 until it is positioned distal of a target site 84, with the proximal end of the positioning guide wire remaining outside the patient for manipulation by the physician. The catheter distal section is then advanced over the positioning guide wire until the deployment tube end port 35 is advanced to and positioned at the target site. Up to this point, the deployment guide wire 112 resides in the deployment tube (within the deployment wire lumen distal section 80—FIG. 7) so that the distal end of the deployment guide wire preferably is near deployment tube end port. This method of delivery prevents the two guide wires from wrapping around each other, the deployment guide wire 112 being protected by the deployment tube 30 of the catheter assembly during positioning of the catheter distal section 74.

Figure 17:
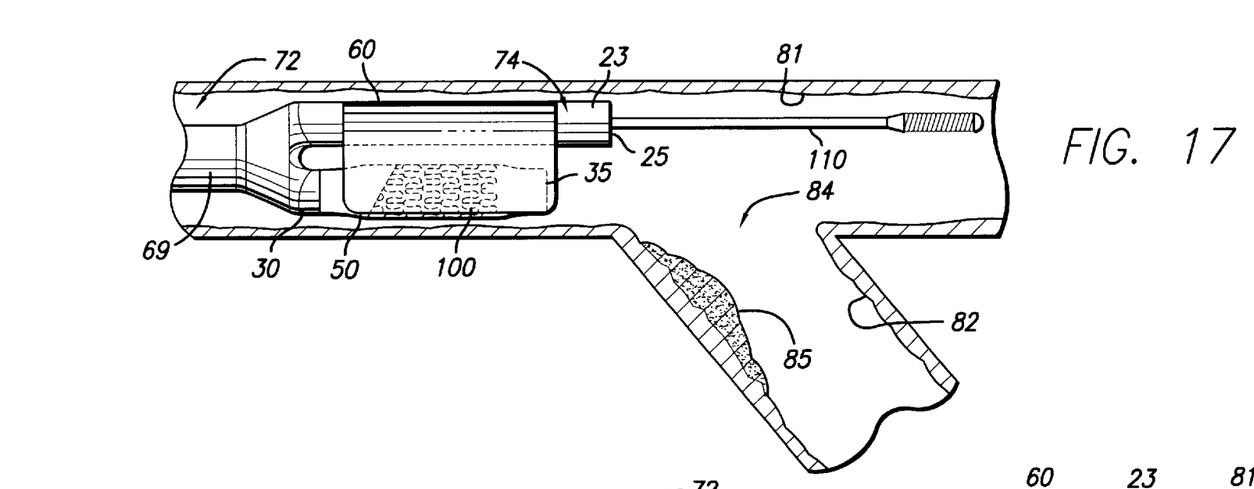
FIG. 17 is a longitudinal plan view of a catheter distal section as it is delivered over a positioning guide wire toward an ostium of a side branch vessel.
Figure 18:
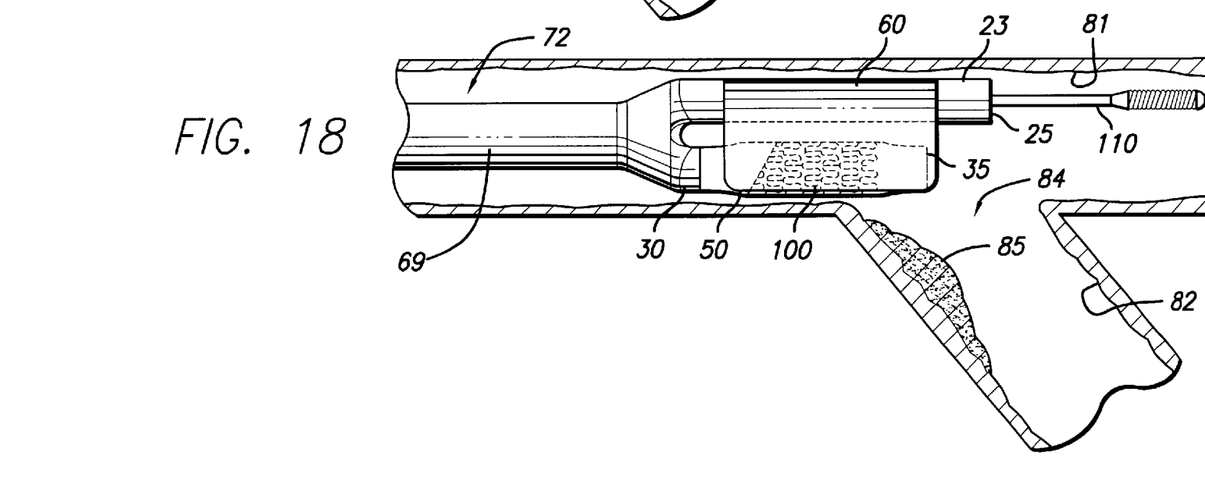
FIG. 18 is a longitudinal plan view of a catheter distal section positioned at an ostium of a side branch vessel showing a restraining member correctly oriented for proper deployment of an angulated stent into a side branch vessel.
Figure 19:
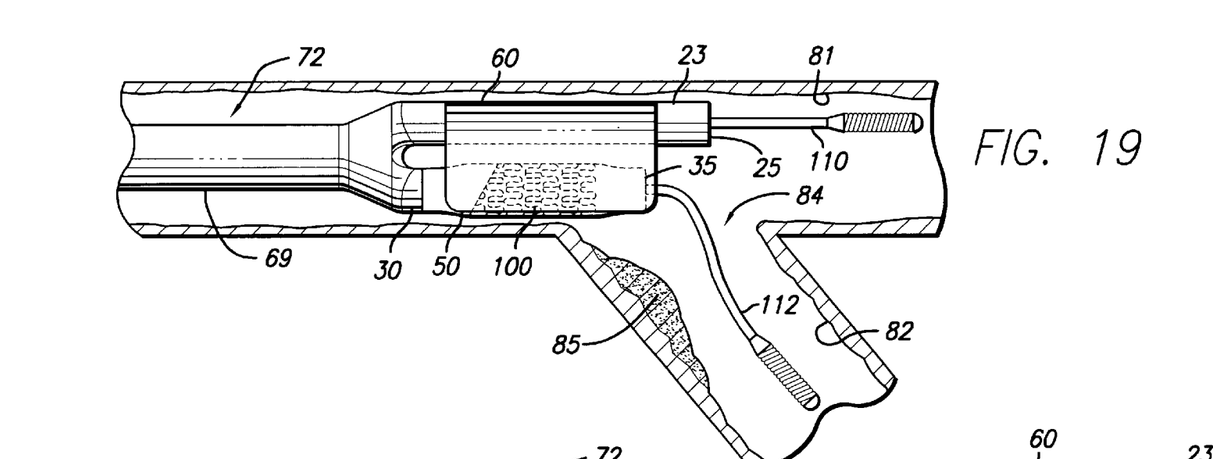
FIG. 19 is a longitudinal plan view of a catheter distal section positioned at an ostium of a side branch vessel showing a deployment guide wire maneuvered into the side branch vessel.

As shown in FIG. 17, the catheter 70 is advanced to the target site 84, once the catheter distal section 74 has been advanced to a location slightly proximal to the target area (FIG. 18), extension of the deployment tube 30 into the branch vessel 82 can only occur if the catheter is in the correct orientation having the U-shaped member 60 (or sheath with slit) oriented such that the opening 68 of the U-shaped member is directed to and corresponds with the side branch vessel. Where proper orientation is achieved, the deployment tube having the angulated stent mounted thereon may be maneuvered into the side branch vessel. As shown in FIG. 19, the distal end of deployment guide wire 112 is then maneuvered and advanced into the side branch vessel 82 by having the physician push the proximal end of the deployment guide wire from outside the patient's body. The distal end of the deployment guide wire travels through the deployment tube, out the deployment tube end port 35, where the wire is maneuvered into the side branch vessel. Possibly, some rotation and longitudinal displacement of the catheter may be needed in order to advance the deployment guide wire into the side branch vessel.

Figure 20:
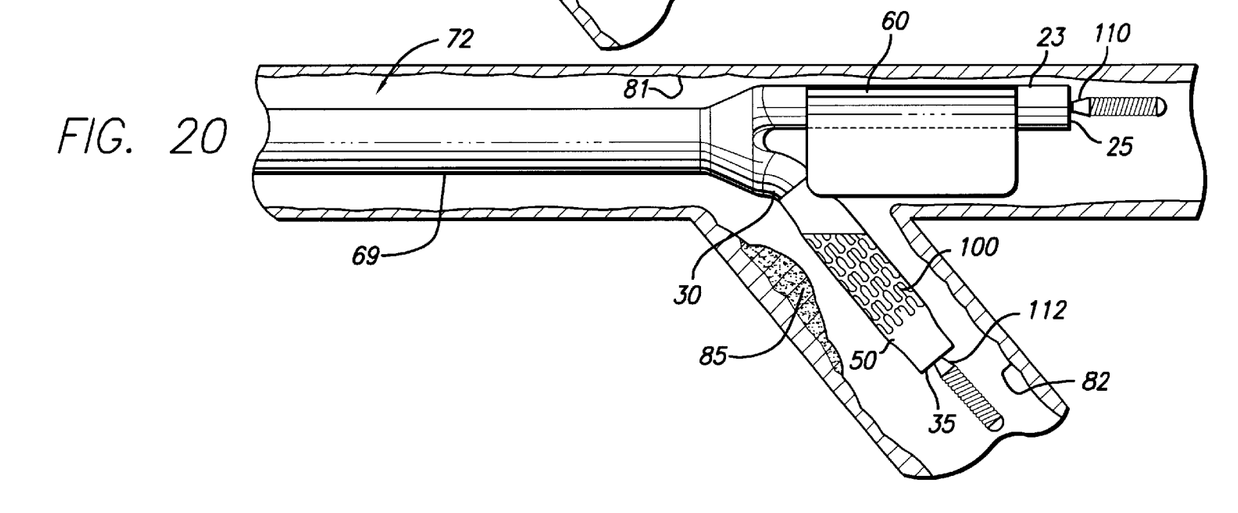
FIG. 20 is a longitudinal plan view of a catheter distal section slightly advanced beyond an ostium of a side branch vessel having a deployment tube advanced over a deployment guide wire and positioned for proper deployment of an angulated stent.

As shown in FIG. 20, after the deployment guide wire 112 is advanced into side branch vessel 82, the physician further advances catheter 70 in the distal direction. This further advancement of the catheter causes the advancement of the deployment tube 30, with the angulated stent 100 mounted on the expandable member 50 of the deployment tube, over the deployment guide wire into the side branch vessel. Thereafter, the catheter 70 is advanced distally, causing the deployment tube to advance deeper into the side branch vessel until the angulated stent is aligned with the ostium of the side branch vessel. Because the angulated stent is pre-mounted with the proper orientation coinciding with the orientation of the side branch vessel, once proper translational positioning is achieved, the stent is deployed by expanding the expandable member 50 (inflating the dilatation balloon), thereby causing the stent to expand and engage against the walls of the side branch vessel (FIG. 21).

Again it is noted that extension of the deployment tube 30 into the side branch vessel 82 is possible only where the catheter 70 is correctly oriented at the target area 84. Because the stent 100 is pre-mounted in such a way that it's orientation coincides with the orientation of the side branch vessel 82, once the catheter is in the correct orientation at the target area to allow the deployment tube to enter the side branch, the angulated stent will also be in the correct orientation for proper deployment.

Figures 21, 22:
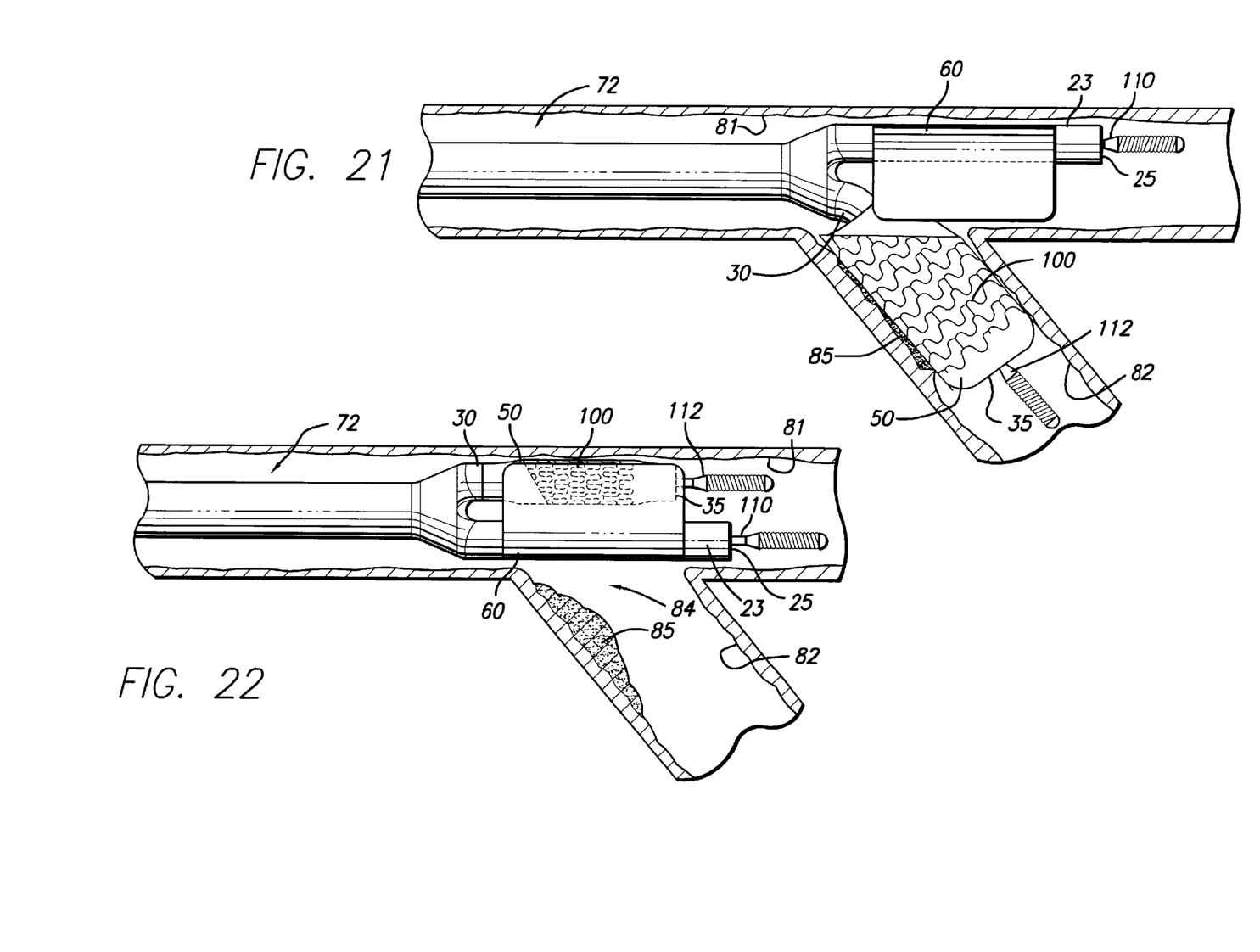
FIG. 21 is a longitudinal plan view of a catheter distal section slightly advanced beyond an ostium of a side branch vessel having a deployment tube advanced over a deployment guide wire as the expandable member is expanded to deploy an angulated stent in the proper orientation.
FIG. 22 is a longitudinal plan view of a catheter distal section positioned at an ostium of a side branch vessel with an incorrect orientation of a U-shaped restraining member, which does not allow for the advancement of a deployment guide wire into the side branch vessel.

As shown in FIG. 22, at times the catheter distal section 74 may be delivered to the target site such that the U-shaped member 60 (or sheath with slit) is incorrectly oriented, and the opening 68 of the U-shaped member (or slit 66 of the sheath) does not correspond to the ostium of the side branch vessel 82. As discussed above, the deployment tube 30 will physically be prevented from being maneuvered into the side branch vessel. Where this is the case, the physician can rotate the proximal end of the catheter 72, which is external to the patient's body, until proper orientation of the catheter distal section is achieved such that the deployment tube is free to move into the side branch vessel.

If the bifurcation between the main vessel 80 and the side branch vessel 82 requires subsequent intervention with a stent or dilatation balloon, then catheter assembly 70 would be withdrawn after rotation into position, leaving both the positioning wire 110 and the deployment wire 112 in position. The delivery of one or more devices over these two unwrapped wires would then be possible without encountering wire wrapping problems.

While the invention herein has been described for use in deploying an angulated stent into a side branch vessel, it will be appreciated that this invention can be used in any application where rotational orientation of a balloon or implantable device in a bifurcation is required. Possible alternative uses may include, but are not limited to, drug delivery and sensing applications where the device can be positioned prior to advancing into a target vessel. Therefore, it will be apparent to one of ordinary skilled in the art that the invention can be used in other instances.

Additionally, while several particular forms of the invention have been illustrated and described, it will also be apparent that various modifications can be made without departing from the spirit and scope of the invention. Accordingly, it is not intended that the invention be limited, except as by the appended claims.

What is claimed:

1. A catheter assembly, comprising:
   a Y-shaped catheter having a proximal section and a distal section, wherein the proximal section includes a positioning guide wire lumen and an elongate tubular member having a deployment guide wire lumen;
   a positioning tube configured in the catheter distal section having a positioning wire lumen extending from and aligned with the positioning guide wire lumen of the catheter proximal section;
   a deployment tube configured in the catheter distal section including the elongate tubular member extending from the catheter proximal section, the deployment tube further including an expandable member; and
   a restraining member disposed over the positioning tube and the deployment tube.

2. The assembly of claim 1, wherein an angulated stent is mounted on the expandable member of the deployment tube.

3. The assembly of claim 2, wherein the restraining member is a U-shaped member.

4. The assembly of claim 3, wherein the U-shaped member is fixedly attached to the positioning tube of the catheter assembly distal section.

5. The assembly of claim 4, wherein the U-shaped member is configured from a stiff flexible material.

6. The assembly of claim 5, wherein the stiff but flexible material is selected from the group consisting of polyethylenes, polyurethanes, polyesters and polyamids.

7. The assembly of claim 5, wherein the stiff but flexible material is Nylon 12.

8. The assembly of claim 2, wherein the restraining member is a sheath having a slit.

9. The assembly of claim 8, wherein the slit extends substantially the full length of the sheath.

10. The assembly of claim 9, wherein the sheath encompasses the entire distal section of the catheter.

11. The assembly of claim 10, wherein the sheath is configured from a stiff but flexible material.

12. The assembly of claim 11, wherein the stiff but flexible material is selected from the group consisting of polyethylenes, polyurethanes, polyesters and polyamids.

13. The assembly of claim 11, wherein the stiff but flexible material is Nylon 12.

14. A method of deploying an angulated stent at a target site in the side branch of a vessel bifurcation having a main branch and a side branch, comprising:
   providing a catheter assembly having
      a) a Y-shaped balloon catheter having a proximal section and a distal section, wherein the proximal section includes a positioning guide wire lumen and an elongate tubular member having a deployment guide wire lumen;

b) a positioning tube configured in the catheter distal section having a positioning wire lumen extending from and aligned with the positioning guide wire lumen of the catheter proximal section;

c) a deployment tube configured in the catheter distal section including the elongate tubular member extending from the catheter proximal section and aligned with the deployment guide wire lumen of the catheter proximal section and an expandable member disposed circumferentially about the elongate tubular member;

d) a deployment guide wire extending through the catheter from the proximal section to the distal section through the deployment guide wire lumen and deployment tube; and e) a restraining member disposed over the positioning tube and the deployment tube;

mounting an angulated stent on the expandable member;

advancing a positioning guide wire through the main branch of the vessel until the guide wire is distal of the target site;

delivering the distal section of the catheter assembly over the positioning guide wire to the target site so that the deployment tube corresponds to the orientation of the side branch vessel;

advancing the deployment guide wire out of the deployment tube into the side branch vessel;

advancing the deployment tube over the deployment guide wire into the side branch vessel; and inflating the expandable member to deploy the angulated stent.

15. The method of claim 14, wherein the mounting an angulated stent includes orienting the stent such that it corresponds to the orientation of the side branch vessel.

16. The method of claim 14, further comprising rotating the catheter into a desired orientation within the vessel to correspond to the orientation of the side branch vessel.

17. The method of claim 16, further comprising deflating the expandable member and the step of withdrawing the catheter from the patient, thereby leaving the positioning guide wire and the deployment guide wire within the vessel, without wrapping of the positioning guide wire and the deployment guide wire.

18. The method of claim 17, further comprising withdrawing the deployment guide wire.

* * * * *

UNITED STATES PATENT AND TRADEMARK OFFICE
CERTIFICATE OF CORRECTION

PATENT NO.    : 6,482,211 B1
DATED         : November 19, 2002
INVENTOR(S)   : Steven R. Choi It is certified that error appears in the above-identified patent and that said Letters Patent is hereby corrected as shown below:

Column 12,
Line 42, after "stiff", add -- but --.

Signed and Sealed this

First Day of April, 2003

JAMES E. ROGAN
*Director of the United States Patent and Trademark Office*